ered the United States Patent

(12) United States Patent
Liu et al.

(10) Patent No.: US 7,608,737 B2
(45) Date of Patent: Oct. 27, 2009

(54) NAPHTHYL(ETHYL)ACETAMIDES

(75) Inventors: Julie F. Liu, Lexington, MA (US); Roger Tung, Lexington, MA (US)

(73) Assignee: Concert Pharmaceuticasl Inc., Lexington, MA (US)

( * ) Notice: Subject to any disclaimer, the term of this patent is extended or adjusted under 35 U.S.C. 154(b) by 0 days.

(21) Appl. No.: 12/112,722

(22) Filed: Apr. 30, 2008

(65) Prior Publication Data
US 2008/0280908 A1    Nov. 13, 2008

Related U.S. Application Data

(60) Provisional application No. 60/915,148, filed on May 1, 2007, provisional application No. 60/639,110, filed on May 21, 2007.

(51) Int. Cl.
*C07C 233/05*    (2006.01)
*A61K 31/16*    (2006.01)
(52) U.S. Cl. ........................ 564/219; 514/630
(58) Field of Classification Search ............... 564/219; 514/630
See application file for complete search history.

(56) References Cited

U.S. PATENT DOCUMENTS

| | | | |
|---|---|---|---|
| 5,225,442 | A | 7/1993 | Andrieux et al. |
| 5,304,121 | A | 4/1994 | Sahatjian |
| 5,318,994 | A | 6/1994 | Andrieux et al. |
| 5,591,775 | A * | 1/1997 | Depreux et al. ............. 514/580 |
| 5,886,026 | A | 3/1999 | Hunter et al. |
| 6,099,562 | A | 8/2000 | Ding et al. |
| 6,803,031 | B2 | 10/2004 | Rabinowitz et al. |
| 7,014,866 | B2 | 3/2006 | Infeld et al. |
| 2006/0079502 | A1 | 4/2006 | Lang |
| 2006/0094744 | A1 | 5/2006 | Maryanoff et al. |
| 2006/0199805 | A1 | 9/2006 | Pyke et al. |

FOREIGN PATENT DOCUMENTS

| | | |
|---|---|---|
| EP | 1 564 202 | 8/2005 |
| EP | 1 769 798 | 4/2007 |
| WO | WO 2005/002562 | 1/2005 |
| WO | WO 2005/077887 | 8/2005 |
| WO | WO 2006/086978 * | 8/2006 |
| WO | WO 2006/096435 | 9/2006 |
| WO | WO 2006/111653 | 10/2006 |
| WO | WO 2007/028904 | 3/2007 |

OTHER PUBLICATIONS

Kushner et al, Can. J. Physiol. Pharmacolo. 77: 79-88, 1999.*
Adam et al., "Nouveaux ligands naphtaleniques des recepteurs melatoninergiques," *J. Pharm. Belg.*, 1992, 47(4):374-380.
Chu et al., "Synthesis of Naphthalenic melatonin receptor cells," *Synth Comm.*, 2001, 31(4):621-629.

Depreux et al., "Synthesis and structure-activity relationships of novel naphthalenic and bioisosteric related amidic derivatives as melatonin receptor ligands," *J. Med. Chem.*, 1994, 37(20):3231-3239.
Descamps-Francois et al., "Design and synthesis of naphthalenic dimers as selective MT1 melatoninergic ligands," *J. Med. Chem.*, 2003, 46(7):1127-1129.
Dunetz et al., "Synthesis of highly substituted indolines and indoles via intramolecular [4+2] cycloaddition of ynamides and conjugated enynes," *J. Am. Chem. Soc.*, 2005, 127(16):5776-5777.
Felix, "Cleavage of protecting groups with boron tibromide," *J. Org. Chem.*, 1974, 39:1427-1429.
Freireich et al., "Quantitative comparison of toxicity of anticancer agents in mouse, rat, hamster, dog, monkey, and man," *Cancer Chemother. Rep.*, 1966, 50:219-244.
Gannes et al., "Natural abundance variations in stable isotopes and their potential uses in animal physiological ecology," *Comp. Biochem. Physiol. Mol. Integr. Physiol.*, 1998, 119:725-737.
Hayford et al, "Practical synthesis of (Z)-polyaromatic and heteroaromatic vinylacetylenes," *Org. Lett.*, 2005, 7(13):2671-2673.
Hesse et al, "Natriumtriathoxy-aluminumhydride, ein neues reduktionsmittel in der organischen chemie," *Ann. Chem.*, 1957, 607:24-35.
Houston, "Utility of in vitro drug metabolism data in predicting in vivo metabolic clearance," *Biochem Pharmacol.*, 1994, 47:1469-1479.
Houston and Carlile, "Prediction of hepatic clearance from microsomes, hepatocytes, and liver slices," *Drug Metab Rev.*, 1997, 29:891-922.
"Efficacy, safety and tolerability of agomelatine in the treatment of major depressive disorder," [online]. Dated Jul. 25, 2008, 4 pages, <http://clinicaltrials.gov/ct/show/NCT00411099>.
Hudlicky, *Reductions in Organic Chemistry*, 1984, John Wiley and Sons, New York, New York, pp. 173-174.
Iwatsubo et al., "Prediction of in vivo drug metabolism in the human liver from in vitro metabolism data," *Pharmacol Ther.*, 1997, 73:147-171.
Lave et al., "The use of human hepatocytes to select compounds based on their expected hepatic extraction ratios in humans," *Pharm Res.*, 1997, 14:152-155.
Loo et al., "A double-blind trial of S-20098 in patients with major depressive or bipolar II disorders: dose-ranging study," *Int. J. Neuropsychopharmacol.*, 2002, 5(Suppl. 1):Abst P.3.E.033.
MacKenzie et al, "Synthesis of the bacterial coenzyme methoxatin," *Tetrahedron*, 1986, 42:3259-3268.
Mewshaw et. al., "ERbeta ligands. 3. Exploiting two binding orientations of the 2-phenylnaphthalene scaffold to achieve ERbeta selectivity," *J. Med. Chem.*, 2005 48(12):3953-3979.
Nystrom, "Reduction of organic compounds by mixed hydrides I. Nitriles," *J. Am. Chem. Soc.*, 1955, 77:2544-2545.

(Continued)

*Primary Examiner*—Shailendra Kumar
(74) *Attorney, Agent, or Firm*—Fish & Richardson P.C.

(57) ABSTRACT

This disclosure relates to novel melatonin analogues or naphthyl(ethyl)acetamides, their derivatives, pharmaceutically acceptable salts, solvates, and hydrates thereof. This disclosure also provides compositions comprising a compound of this disclosure and the use of such compositions in methods of treating diseases and conditions that are beneficially treated by administering a dual melatoninergic agonist and serotoninergic antagonist.

18 Claims, No Drawings

OTHER PUBLICATIONS

Obach, "Prediction of human clearance of twenty-nine drugs from hepatic microsomal intrinsic clearance data: An examination of in vitro half-life approach and nonspecific binding to microsomes," *Drug Metab. Disp.*, 1999, 27:1350-1359.

*Scientific Tables*, Geigy Pharmaceuticals, Ardsley, N.Y., 1970, 537.

Suzuki et al, "Synthesis and DNA damaging ability of enediyne-polyamine conjugates," *Tetrahedron Lett.*, 2004, 45(9):1955-1959.

Vickery et al, "Selective 0-Demethylation of Catechol Ethers, Comparison of Boron Tribromide and Iodotrimethylsilane," *J. Org. Chem.*, 1979, 44:4444-4446.

Wada et al., *Seikagaku*, 1994, 66:15-29.

Xu et al, "Site-specific preparation of 3-fluoro-1-substituted-naphthalenes via a novel base-catalyzed cyclization reaction from (E)-monofluoroenynes," *Org. Lett.*, 2006, 8(12):2555-2558.

Yous et al., "Novel naphthalenic ligands with high affinity for the melatonin receptor," *J. Med. Chem.*, 1992, 35(8):1484-1486.

"Refusal CHMP Assessment Report for Valdoxan," *Euro. Medicines Agency*, 2006, 1-39.

Burm et al., "Pharmacokinetics of Lidocaine and Bupivacaine and Stable Isotope Labelled Analogues: A Study in Healthy Volunteers," *Bio. & Drug Disp.*, 1988, 9: 85-95.

Fisher et al., "The Complexities Inherent in Attempts to Decrease Drug Clearance by Blocking Sites of CYP-mediated Metabolism," *Curr. Opin. Drug Discov. Dev.*, 2006, 9(1):101-109.

Foster et al., "Deuterium isotope effects in the metabolism of drugs and xenobiotics," *Adv. In Drug Res.*, 1985, 14: 2-40.

Helfenbein et al., "Isotopic Effect Study of Propofol Deuteration on the Metabolism, Activity, and Toxicity of the Anesthetic," *J. Med. Chem.*, 2002, 45: 5806-5808.

Kushner et al., "Pharmacological Uses and Perspectives of Heavy Water and Deuterated Compounds," *Can. J. Physiol. Pharmacol.*, 1999, 77:79-88.

Ling et al., "Deuterium isotope effects on toluene metabolism. Product release as a rate-limiting step in cytochrome P-450 catalysis." *Biochem. Biophys. Res. Comm.*, 1989, 160(2): 844-849.

Ma et al., "Metabolism of Melatonin by Human Cytochromes P450," *Drug. Met. And Disposition*, 2005, 33(4): 489-494.

Mamada et al., "Pharmacokinetic Equivalence of Deuterium-Labeled and Unlabeled Phenytoin," *Drug. Met. And Disposition*, 1986, 14(4): 509-511.

Obach, "Mechanism of Cytochrome P4503A4- and 2D6-Catalyzed Dehydrogenation of Ezlopitant as Probed with Isotope Effects Using Five Deuterated Analogs," *Drug Met. And Disposition*, 2001, 29(12): 1599-1607.

* cited by examiner

NAPHTHYL(ETHYL)ACETAMIDES

CROSS-REFERENCE TO RELATED APPLICATION

This application claims the benefit of priority under 35 U.S.C. § 119 to U.S. Provisional Application Ser. Nos. 60/915,148, filed May 1, 2007, and 60/639,110, filed May 21, 2007, the entire contents of which are incorporated by reference in their entirety herein.

BACKGROUND

This disclosure relates to novel melatonin analogues or naphthyl(ethyl)acetamides, their derivatives, pharmaceutically acceptable salts, solvates, and hydrates thereof. This disclosure also provides compositions comprising a compound of this disclosure and the use of such compositions in methods of treating diseases and conditions that are beneficially treated by administering a dual melatoninergic agonist and serotoninergic antagonist.

Agomelatine, known by the chemical name N-[2-(7-methoxy-1-napthyl)ethyl]acetamide, acts by stimulating MT1 and MT2 receptors and blocking 5-HT2B and 5-HT2C receptors.

Agomelatine is currently in phase III clinical trials for major depressive disorder (http://clinicaltrials.gov/ct/show/NCT00411099) and has been indicated as useful in the treatment of bipolar disorder, sleep disorder, and anxiety (WO2005002562; and WO 2005077887).

Active metabolites of Agomelatine include the following:

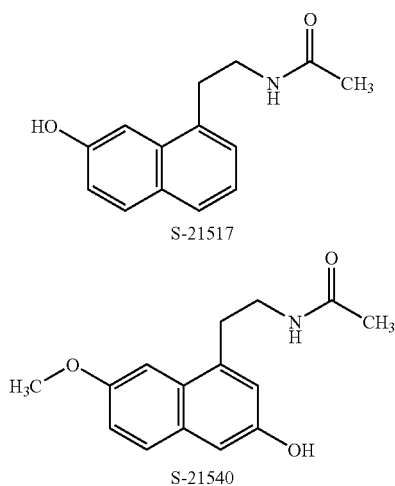

Agomelatine has been found to have a side effect profile similar to placebo. (Loo, H et al., Int J Neuropsychopharmacol, 2002, 5(Suppl. 1):Abst P.3.E.033).

Despite its apparent efficacy, it is desirable to provide a compound that has the beneficial activities of Agomelatine and may also have other benefits, e.g., reduced adverse side effects, with a decreased metabolic liability, to further extend its pharmacological effective life, enhance patient compliance and, potentially, to decrease population pharmacokinetic variability and/or decrease its potential for dangerous drug-drug interactions.

DETAILED DESCRIPTION

Definitions

The terms "ameliorate" and "treat" are used interchangeably and include therapeutic and/or prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of Agomelatine will inherently contain small amounts of deuterated and/or $^{13}C$-containing isotopologues. The concentration of naturally abundant stable hydrogen and carbon isotopes, notwithstanding this variation, is small and immaterial as compared to the degree of stable isotopic substitution of compounds of this disclosure. See, for instance, Wada E et al., Seikagaku 1994, 66:15; Ganes L Z et al., Comp Biochem Physiol Mol Integr Physiol, 1998, 119: 725. In a compound of this disclosure, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that has the same chemical structure and formula as a specific compound of this invention, with the exception of the isotopic composition at one or more positions, e.g., H vs. D. Thus an isotopologue differs from a specific compound of this invention in the isotopic composition thereof.

The term "compound," as used herein, is also intended to include any salts, solvates or hydrates thereof.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present disclosure (e.g., compounds of Formula A or Formula I), may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"Tert", "t", and "t-" each refer to tertiary.

"US" refers to the United States of America.

"FDA" refers to Food and Drug Administration.

"NDA" refers to New Drug Application.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present disclosure provides a compound of Formula A:

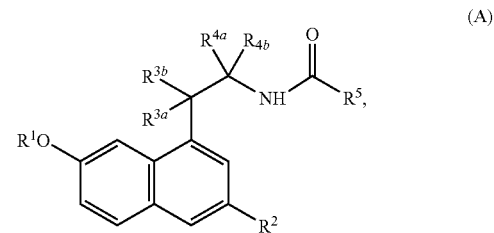

(A)

or a pharmaceutically acceptable salt, solvate or hydrate thereof, wherein:

$R^1$ is selected from H, $CH_3$, $CH_2D$, $CHD_2$ and $CD_3$;

$R^2$ is selected from OH, H, D and F;

each of $R^{3a}$, $R^{3b}$, $R^{4a}$, and $R^{4b}$ is independently selected from H and D;

and $R^5$ is selected from $CH_3$, $CH_2D$, $CHD_2$ and $CD_3$; and at least one R comprises a deuterium atom.

In certain embodiments of Formula A:

a) $R^1$ is selected from $CH_3$, $CD_3$ and H;

b) $R^2$ is selected from H and D;

c) each $R^3$ is the same;

d) each $R^4$ is the same; or e) $R^5$ is selected from $CH_3$ and $CD_3$.

In a more specific embodiment, a compound of Formula A has the properties set forth in two or more of a) through e), above.

In another specific embodiment, each of $R^{3a}$, $R^{3b}$, $R^{4a}$ and $R^{4b}$ is the same. In an even more specific embodiment, each of $R^{3a}$, $R^{3b}$, $R^{4a}$ and $R^{4b}$ is the same and the compound has the properties set forth in one or more of a), b) and e), above. In another specific embodiment each of $R^{3a}$, $R^{3b}$, $R^{4a}$, and $R^{4b}$ is H. In still another more specific embodiment, each of $R^{3a}$, $R^{3b}$, $R^{4a}$, and $R^{4b}$ is H and the compound has the properties set forth in one or more of a), b) and e), above.

In an even more specific embodiment, each of $R^{3a}$, $R^{3b}$, $R^{4a}$, and $R^{4b}$ is H; and $R^5$ is $CH_3$, the compound having the Formula I:

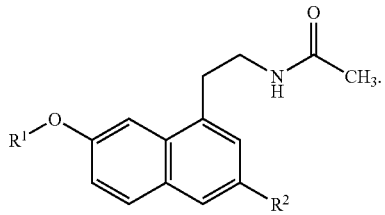

In one embodiment of Formula I, $R^1$ is selected from $CH_3$, $CHD_2$ and $CD_3$. In a more specific embodiment, $R^1$ is selected from $CH_3$ and $CD_3$.

According to another embodiment of Formula I, $R^2$ is selected from H and D.

In one specific embodiment of Formula I, $R^1$ is selected from H, $CH_3$ and $CD_3$; and $R^2$ is selected from H and D.

In another embodiment of Formula I, $R^2$ is selected from F and OH.

In a more specific embodiment, the compound of Formula A is selected from any one of the compounds (Cmpd) set forth in Table 1 (below):

TABLE 1

Exemplary Embodiments of Formula A

| Cmpd | $R^1$ | $R^2$ | Each $R^3$ | Each $R^4$ | $R^5$ |
|---|---|---|---|---|---|
| 100 | $CH_3$ | D | H | H | $CH_3$ |
| 101 | $CD_3$ | H | H | H | $CH_3$ |
| 102 | $CD_3$ | D | H | H | $CH_3$ |
| 103 | H | D | H | H | $CH_3$ |
| 104 | $CD_3$ | OH | H | H | $CH_3$ |
| 105 | $CD_3$ | F | H | H | $CH_3$ |
| 106 | $CD_3$ | H | H | H | $CD_3$ |
| 107 | $CD_3$ | H | D | D | $CD_3$ |

In an even more specific embodiment, a compound of Formula A is selected from:

Compound 101

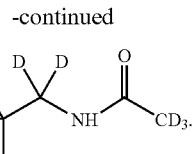

Compound 106

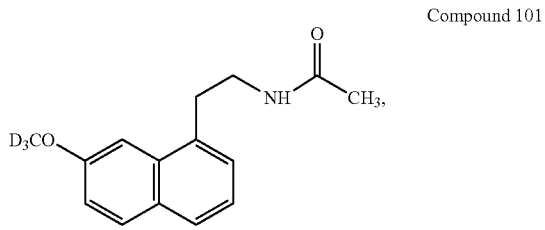

-continued

Compound 107

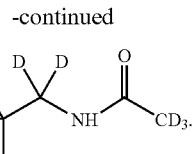

In another embodiment, any atom not designated as deuterium in any of the embodiments set forth above is present at its natural isotopic abundance.

In another set of embodiments, the compound of Formula A or Formula I is isolated or purified, e.g., the compound of Formula A or Formula I is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues of Formula A or Formula I present, respectively. Thus, in some embodiments, a composition comprising a compound of Formula A or Formula I can include a distribution of isotopologues of the compound, provided at least 50% of the isotopologues by weight are the recited compound.

In some embodiments, any position in the compound of Formula A or Formula I designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula A or Formula I. Thus, in some embodiments, a composition comprising a compound of Formula A or Formula I can include a distribution of isotopologues of the compound, provided at least 45% of the isotopologues include a D at the designated position(s).

In some embodiments, a compound of Formula A or Formula I is "substantially free of" other isotopologues of the compound, e.g., less than 50%, less than 25%, less than 10%, less than 5%, less than 2%, less than 1%, or less than 0.5% of other isotopologues are present.

The synthesis of compounds of Formula A or Formula I can be readily achieved by synthetic chemists of ordinary skill. Relevant procedures and intermediates are disclosed, for instance in European Patent Appln. 1564202; U.S. Pat. No. 5,318,994; Descamps-Francois, C et al., J Med Chem 2003, 46(7):1127-1129. Chu, G-H et al., Synth Comm 2001, 31(4): 621-629; Adam, G et al., J Pharm Belg 1992, 47(4):374-80; Yous, S et al., J Med Chem 1992, 35(8):1484-6; and Depreux, P et al., J Med Chem 1994, 37(20):3231

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

EXEMPLARY SYNTHESIS

Convenient methods for synthesizing compounds of this disclosure are depicted in Schemes I-III.

Scheme I

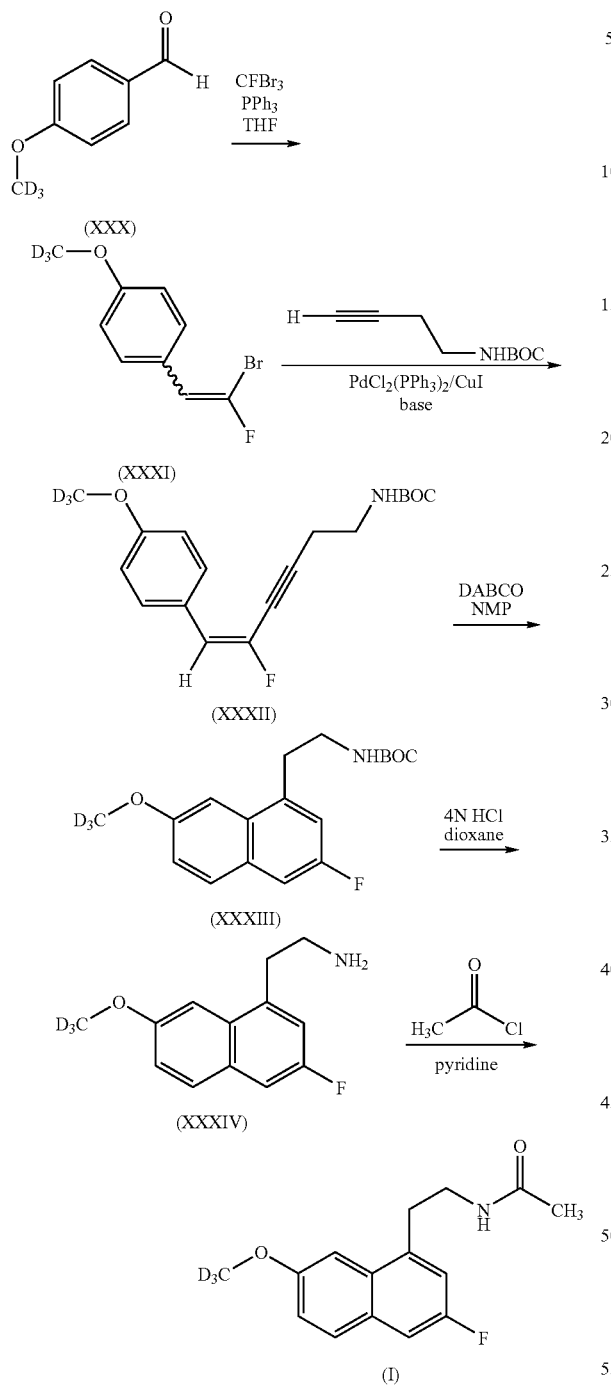

Scheme II

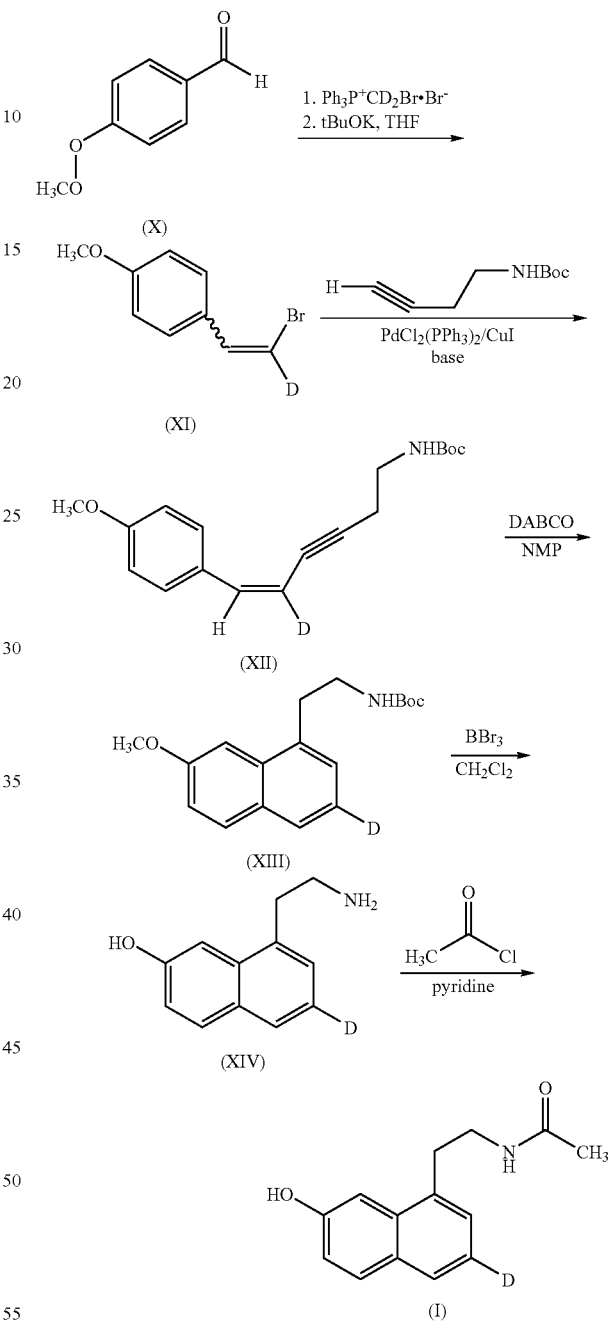

Am Chem Soc, 2005, 127(16):5776-5777; and Suzuki, I et al., Tet Lett, 2004, 45(9):1955-1959.

An appropriately-deuterated aldehyde XXX is converted to styrene derivative XXXI. Sonogashira coupling with the desired alkyne provides compound XXXII, which is cyclized to yield the desired intermediate heterocycle XXXIII. Compound XXXIII is deprotected to produce the amine XXXIV, which is then modified to produce a compound of Formula A or Formula I, wherein $R^1$ is deuteromethyl and $R^2$ is fluorine. General procedures for this synthetic route are found in: Xu, J et al., Org Lett, 2006, 8(12):2555-2558; Dunetz, J R et al., J P-anisaldehyde (X) is converted to styrene-derivative XI. Sonogashira coupling with the desired protected alkyne provides compound XII, which is then cyclized to the desired substituted intermediate naphthalene XIII. This intermediate (XIII) is then treated with boron tribromide to simultaneously remove the Boc and methyl ether groups to afford XIV. Acetylation of XIV gives a compound of Formula A or Formula I where $R^1$ is H. General procedures for this synthetic route are found in Xu, J et al, Org Lett 2006, 8(12): 2555-2558; Dunetz, J R et al, J Am Chem Soc 2005, 127(16):5776-5777; Suzuki, I et al, Tet Lett 2004, 45(9):1955-1959; Hayford, A et al, Org Lett 2005, 7(13):2671-2673; Felix, A M, J Org Chem 1974, 39:1427; and Vickery, E H et al, J Org Chem 1979, 44:4444.

Alternatively, compound XIII can be treated with 4N HCl/dioxane to remove the Boc, while retaining the methyl ether. Acetylation of the resulting product produces a compound of Formula A or Formula I where $R^1$ is methyl and $R^2$ is D.

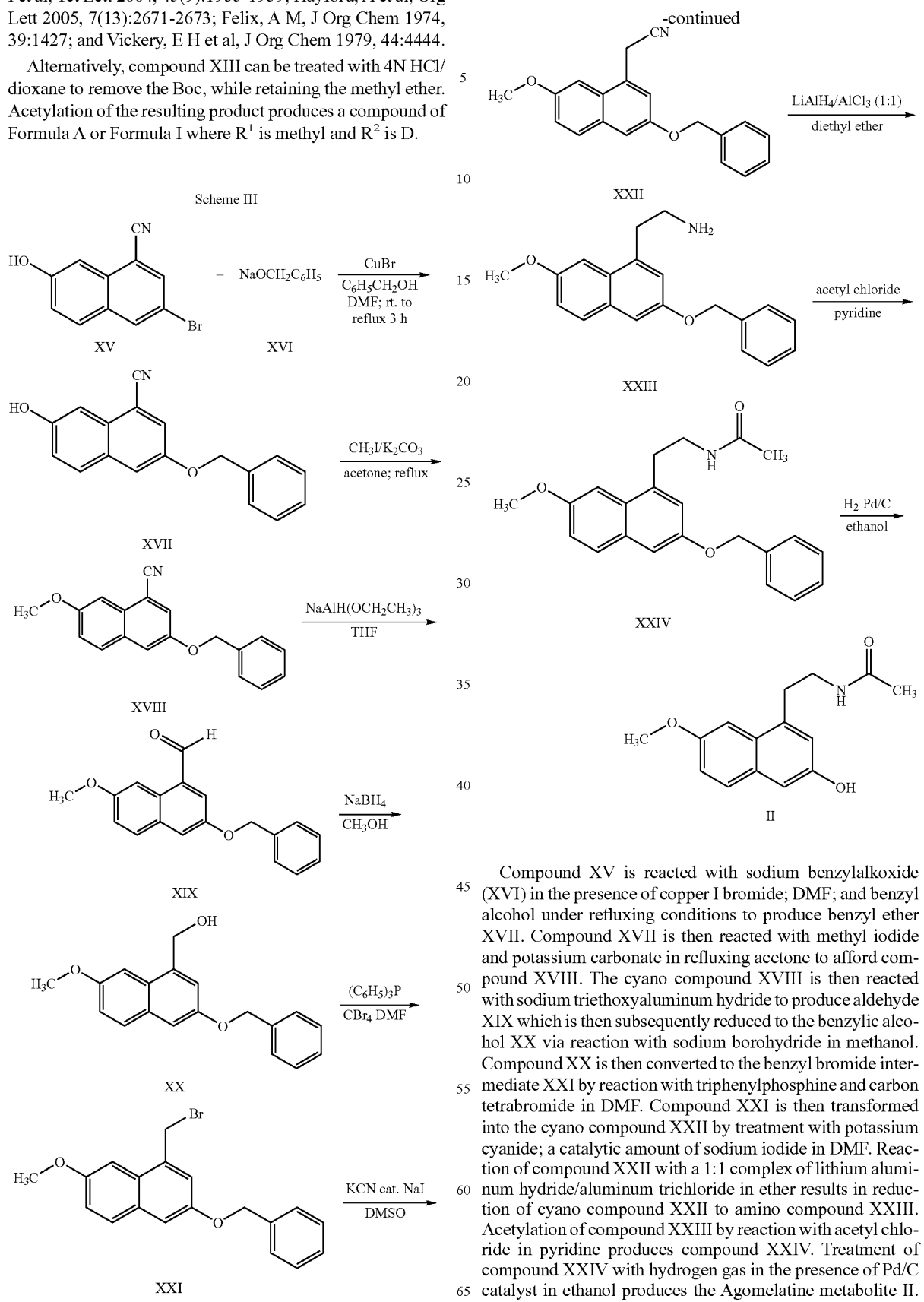

Compound XV is reacted with sodium benzylalkoxide (XVI) in the presence of copper I bromide; DMF; and benzyl alcohol under refluxing conditions to produce benzyl ether XVII. Compound XVII is then reacted with methyl iodide and potassium carbonate in refluxing acetone to afford compound XVIII. The cyano compound XVIII is then reacted with sodium triethoxyaluminum hydride to produce aldehyde XIX which is then subsequently reduced to the benzylic alcohol XX via reaction with sodium borohydride in methanol. Compound XX is then converted to the benzyl bromide intermediate XXI by reaction with triphenylphosphine and carbon tetrabromide in DMF. Compound XXI is then transformed into the cyano compound XXII by treatment with potassium cyanide; a catalytic amount of sodium iodide in DMF. Reaction of compound XXII with a 1:1 complex of lithium aluminum hydride/aluminum trichloride in ether results in reduction of cyano compound XXII to amino compound XXIII. Acetylation of compound XXIII by reaction with acetyl chloride in pyridine produces compound XXIV. Treatment of compound XXIV with hydrogen gas in the presence of Pd/C catalyst in ethanol produces the Agomelatine metabolite II. The synthetic procedure for the preparation of compound XV follows the published procedure of Mewshaw, R E et. al. J.

Med. Chem. 2005 48(12) 3953-3979. Procedures from the same publication were also used to produce compound XVII. Reaction conditions shown in Scheme III were also adapted from the following literature references: MacKenzie, A R et al *Tetrahedron* 1986, 42:3259; Hudlicky, M, Reductions in Organic Chemistry, John Wiley and Sons, New York, N.Y. 1984, 173-174; Hesse, G et al, Ann Chem 1957, 607:24; and Nystrom, R B, J Am Chem Soc 1955, 77:2544

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula A or Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this disclosure are only those that result in the formation of stable compounds.

Compositions

The disclosure also provides pyrogen-free compositions comprising an effective amount of a compound of Formula A or Formula I (e.g., including any of the formulae herein), or a pharmaceutically acceptable salt, solvate, or hydrate of said compound; and an acceptable carrier. Preferably, a composition of this disclosure is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active.

Where an organ or tissue is accessible because of removal from the patient, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with a compound having the same mechanism of action as Agomelatine. Such agents include those indicated as being useful in combination with Agomelatine, including but not limited to, those described in WO 2007028904 and WO 2005002562.

Preferably, the second therapeutic agent is an agent useful in the treatment or prevention of a disease or condition selected from depression, anxiety, bipolar disorder, and sleep disorder.

In one embodiment, the second therapeutic agent is selected from Reboxetine mesilate, Citalopram hydrobromide, Fluvoxamine maleate, Paroxetine, Fluoxetine hydrochloride, Escitalopram oxalate, and Sertraline hydrochloride.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this disclosure can range from 0.25 to 500 mg per day. In more specific embodiments the range is from 2.5 to 250 mg/day, or from 5 to 100 mg/day or from 25 to 50 mg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for Agomelatine.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Methods of Treatment

In another embodiment, the disclosure provides a method of stimulating MT1 and MT2 receptors and blocking 5-HT2B and 5-HT2C receptors in a cell, comprising contacting a cell with one or more compounds of Formula A or Formula I herein.

According to another embodiment, the disclosure provides a method of treating a subject suffering from, or susceptible to, a disease that is beneficially treated by Agomelatine comprising the step of administering to said subject an effective amount of a compound or a composition of this disclosure. Such diseases are well known in the art and are disclosed in, but not limited to the following patents and published applications: WO 2007028904, WO 2005002562, WO 2005077887, WO 2006111653, WO 2006096435, and US 2006199805. Such diseases include, but are not limited to, depression, anxiety, bipolar disorder, and sleep disorders.

In one particular embodiment, the method of this disclosure is used to treat a subject suffering from or susceptible to a disease or condition selected from depression and bipolar disorder.

Methods delineated herein also include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with Agomelatine. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include co-administering a compound of Formula A or Formula I and a second therapeutic agent for treatment of the following conditions: depression (Reboxetine mesilate); anxiety and depression (Citalopram hydrobromide, Fluvoxamine maleate, Paroxetine, Fluoxetine hydrochloride, Escitalopram oxalate, and Sertraline hydrochloride).

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent or any compound of this disclosure to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In yet another aspect, the disclosure provides the use of a compound of Formula A or Formula I alone or together with one or more of the above-described second therapeutic agents in the manufacture of a medicament, either as a single composition or as separate dosage forms, for treatment or prevention in a subject of a disease, disorder or symptom set forth above. Another aspect of the disclosure is a compound of Formula A or Formula I for use in the treatment or prevention in a subject of a disease, disorder or symptom thereof delineated herein.

Diagnostic Methods and Kits

The compounds and compositions of this disclosure are also useful as reagents in methods for determining the concentration of Agomelatine in solution or biological sample such as plasma, examining the metabolism of Agomelatine and other analytical studies.

According to one embodiment, the disclosure provides a method of determining the concentration, in a solution or a biological sample, of Agomelatine, comprising the steps of:
 a) adding a known concentration of a compound of Formula A or Formula I to the solution of biological sample;
 b) subjecting the solution or biological sample to a measuring device that distinguishes Agomelatine from a compound of Formula A or Formula I;
 c) calibrating the measuring device to correlate the detected quantity of the compound of Formula A or Formula I with the known concentration of the compound of Formula A or Formula I added to the biological sample or solution; and
 d) measuring the quantity of Agomelatine in the biological sample with said calibrated measuring device; and
 e) determining the concentration of Agomelatine in the solution of sample using the correlation between detected quantity and concentration obtained for a compound of Formula A or Formula I.

Measuring devices that can distinguish Agomelatine from the corresponding compound of Formula A or Formula I include any measuring device that can distinguish between two compounds that differ from one another only in isotopic abundance. Exemplary measuring devices include a mass spectrometer, NMR spectrometer, or IR spectrometer.

In another embodiment, a method for determining the amount of Agomelatine in a solution or a biological sample is provided, comprising:
 a) adding a known amount of a compound of Formula A or Formula I to the solution or biological sample;
 b) detecting at least one signal for a compound of Formula A or Formula I and at least one signal for Agomelatine in a measuring device that is capable of distinguishing the two compounds;
 c) correlating the at least one signal detected for a compound of Formula A or Formula I with the known amount of the compound of Formula A or Formula I added to the solution or the biological sample; and
 d) determining the amount of Agomelatine in the solution or biological sample using the correlation between the at least one signal detected of the compound of Formula A or Formula I and the amount added to the solution or biological sample of a compound of Formula A or Formula I.

In another embodiment, the disclosure provides a method of evaluating the metabolic stability of a compound of Formula A or Formula I comprising the steps of contacting the compound of Formula A or Formula I with a metabolizing enzyme source for a period of time and comparing the amount of the compound of Formula A or Formula I with the metabolic products of the compound of Formula A or Formula I after the period of time.

In a related embodiment, the disclosure provides a method of evaluating the metabolic stability of a compound of Formula A or Formula I in a subject following administration of the compound of Formula A or Formula I. This method comprises the steps of obtaining a serum, blood, tissue, urine or feces sample from the subject at a period of time following the administration of the compound of Formula A or Formula I to the subject; and comparing the amount of the compound of Formula A or Formula I with the metabolic products of the compound of Formula A or Formula I in the serum, blood, tissue, urine or feces sample.

The present disclosure also provides kits for use to treat depression and bipolar disorder. These kits comprise (a) a pharmaceutical composition comprising a compound of Formula A or Formula I or a salt, hydrate, or solvate thereof, wherein said pharmaceutical composition is in a container; and (b) instructions describing a method of using the pharmaceutical composition to treat depression and bipolar disorder.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kits of this disclosure may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this disclosure may comprise in a separate vessel of container a pharmaceutical composition comprising a second therapeutic agent, such as one of those listed above for use for co-administration with a compound of this disclosure.

EXAMPLES

Example 1

Synthesis of N-(2-(7-(methoxy-d$_3$)-naphthalen-1-yl) ethyl)acetamide-d$_3$ (106). Compound 106 was prepared as outlined in Scheme IV below. Details of the synthesis are set forth below.

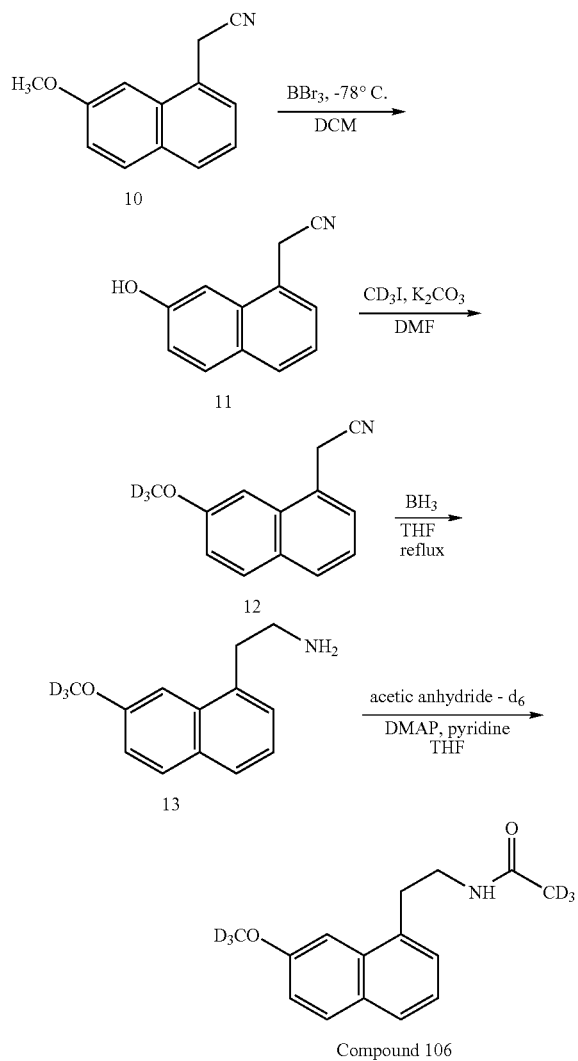

Scheme IV: Preparation of N-(2-(7-(methoxy-d$_3$)-naphthalen-1-yl)ethyl)acetamide-d$_3$(106).

Synthesis of 2-(7-hydroxynaphthalen-1-yl)acetonitrile (11). To a solution of nitrile 10 (0.500 g, 2.5 mmol) in DCM (20 mL) at −78° C. was added BBr$_3$ (0.337 mL, 6.3 mmol, 2.5 eq) with stirring. The reaction mixture was stirred at −78° C. for 1 h then poured into cold (0° C.) CH$_3$OH (100 mL). The resulting solution was concentrated under reduced pressure then dried under high vacuum to yield a brown solid. Purification via automated flash column chromatography (90:10:1—CHCl$_3$:CH$_3$OH:NH$_4$OH) afforded intermediate 11 (218 mg, 48% yield).

Synthesis of 2-(7-(methoxy-d$_3$)naphthalen-1-yl)acetonitrile (12). To a solution of alcohol 11 (0.218 g, 1.2 mmol) in DMF (20 mL) was added with stirring, K$_2$CO$_3$ (0.197 g, 1.4 mmol, 1.2 eq) and CD$_3$I (0.164 g, 1.1 mmol, 0.95 eq). The mixture was stirred at RT under N$_2$ overnight followed by the addition of H$_2$O (20 mL) and extraction with EtOAc (2×30 mL). The combined organic layers were washed with brine solution (30 mL), dried over Na$_2$SO$_4$, filtered and concentrated in vacuo to yield the product 12 (206 mg, 86% yield, 95% purity).

Synthesis of 2-(7-(methoxy-d$_3$)naphthalen-1-yl)ethanamine (13). A solution of 12 (0.206 g, 1.0 mmol) in THF (20 mL) was cooled to 0° C. To this solution was added 1.0 M BH$_3$ in THF (2.21 mL, 2.2 mmol, 2.2 eq). The resulting mixture was stirred under an atmosphere of N$_2$ at RT for 1 h, then under reflux conditions for 15 h. The mixture was then cooled to 0° C., and CH$_3$OH was added to quench the reaction. The resulting mixture was stirred under reflux conditions for 1 h. Concentration of the mixture under reduced pressure afforded 13 (236 mg, quantitative yield). Synthesis of N-(2-(7-(methoxy-d$_3$)-naphthalen-1-yl)ethyl)acetamide-d$_3$ (106). To a solution of the amine, 13 (0.236 g, 1.2 mmol) in THF (20 mL) was added pyridine (0.097 mL, 1.2 mmol, 1.0 eq), DMAP (0.141 g, 1.2 mmol, 1.0 eq), and acetic anhydride-d$_6$ (0.120 mL, 1.2 mmol, 1.0 eq) with stirring. The reaction mixture was stirred for 1 h at RT then was concentrated in vacuo and purified by reverse phase HPLC to yield Compound 106 as the formic acid salt (32 mg, 95% purity). $^1$H-NMR (300 MHz, CDCl$_3$): δ 3.24 (t, J=7.6, 2H), 3.61 (dt, J$_1$=7.6, J$_2$=6.2, 2H), 5.52 (bs, 1H), 7.15 (dd, J$_1$=9.1, J$_2$=2.4, 1H), 7.23-7.28 (m, 2H), 7.45 (d, J=2.4, 1H), 7.67 (dd, J$_1$=6.7, J$_2$=2.4, 1H), 7.75 (d, J=9.1, 1H). MS (M+H): 250.

Evaluation of Metabolic Stability

Certain in vitro liver metabolism studies have been described previously in the following references, each of which is incorporated herein in their entirety: Obach, R. S. Drug Metab Disp 1999, 27, p. 1350; Houston, J. B. et al., Drug Metab Rev 1997, 29, p. 891; Houston, J. B. Biochem Pharmacol 1994, 47, p. 1469; Iwatsubo, T et al., Pharmacol Ther 1997, 73, p. 147; and Lave, T. et al., Pharm Res 1997, 14, p. 152.

Microsomal Assay: The metabolic stability of compounds of Formula A or Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L. P. (Exton, Pa.), or XenoTech, LLC (Lenexa, Kans.)). The incubation mixtures are prepared as follows:

| Reaction Mixture Composition | |
|---|---|
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (no test compound is added). The reaction is initiated by the addition of cofactors (not added to the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as agomelatine, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a compound of Formula A or Formula I in 100 mM potassium phosphate buffer (pH 7.4) is incubated at 37° C. in triplicate. Positive controls contain 1 µM of agomelatine instead of a compound of Formula A or Formula I. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in –20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

We claim:

1. A compound of the Formula A:

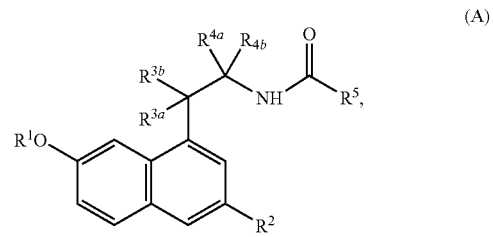

or a pharmaceutically acceptable salt, solvate or hydrate thereof, wherein:
R$_1$ is CD$_3$;
R$_2$ is selected from OH, H, D and F;
each of R$^{3a}$, R$^{3b}$, R$^{4a}$, and R$^{4b}$ is independently selected from H and D; and
R$^5$ is CD$_3$.

2. The compound of claim 1, wherein R$^2$ is selected from H and D.

3. The compound of claim 1, wherein each R$^3$ is the same.

4. The compound of claim 1, wherein each R$^4$ is the same.

5. The compound of claim 4, wherein each of R$^{3a}$, R$^{3b}$, R$^{4a}$, and R$^{4b}$ is the same.

6. The compound of claim 5, wherein each of R$^{3a}$, R$^{3b}$, R$^{4a}$, and R$^{4b}$ is H.

7. The compound of claim 1, wherein the compound is:

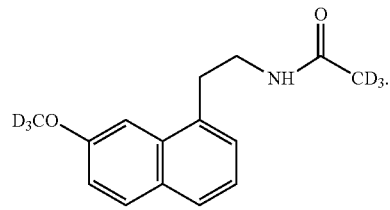

8. The compound of claim 1, wherein the compound is:

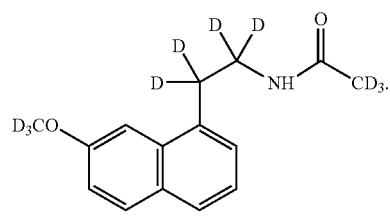

9. The compound of claim 1, wherein any atom not designated as deuterium is present at its natural isotopic abundance.

10. A pyrogen-free composition comprising a compound of claim 1; and an acceptable carrier.

11. The composition of claim 10, wherein the composition is suitable for pharmaceutical administration and said carrier is a pharmaceutically acceptable carrier.

12. The composition of claim 11, additionally comprising a second therapeutic agent.

13. The composition of claim 12, wherein said second therapeutic agent is an agent useful in the treatment or prevention of a disease or condition selected from depression, anxiety, bipolar disorder, and sleep disorder.

14. The composition of claim 13, wherein the second therapeutic agent is selected from reboxetine mesilate, citalopram hydrobromide, fluvoxamine maleate, paroxetine, fluoxetine hydrochloride, escitalopram oxalate, and sertraline hydrochloride.

15. A method of treating a subject suffering from, or susceptible to, a disease selected from depression, anxiety, bipolar disorder, and sleep disorders comprising the step of administering to the subject in need thereof a composition of claim 10.

16. The method of claim 15, wherein the disease or condition selected from depression, and bipolar disorder.

17. The method of claim 15, comprising the additional step of co-administering to the subject in need thereof a second therapeutic agent.

18. The method of claim 17, wherein the second therapeutic agent is selected from:
   a. reboxetine mesilate when the subject is suffering from, or susceptible to depression; and
   b. citalopram hydrobromide, fluvoxamine maleate, paroxetine, fluoxetine hydrochloride, escitalopram oxalate, and/or sertraline hydrochloride when the subject is suffering from, or susceptible to anxiety and depression.

* * * * *

UNITED STATES PATENT AND TRADEMARK OFFICE
CERTIFICATE OF CORRECTION

PATENT NO. : 7,608,737 B2  Page 1 of 1
APPLICATION NO. : 12/112722
DATED : October 27, 2009
INVENTOR(S) : Julie F. Liu et al.

It is certified that error appears in the above-identified patent and that said Letters Patent is hereby corrected as shown below:

Title Page item 73, Assignee, please delete "Concert Pharmaceuticasl" and insert --Concert Pharmaceuticals-- therefor.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,608,737 B2  Page 1 of 2
APPLICATION NO. : 12/112722
DATED : October 27, 2009
INVENTOR(S) : Julie F. Liu It is certified that error appears in the above-identified patent and that said Letters Patent is hereby corrected as shown below:

Title Page, Related U.S. Application Data, please delete "60/639,110" and insert --60/939,110-- therefor;

Title Page, References Cited, Other Publications, Felix reference, please delete "tibromide" and insert --tribromide-- therefor;

Column 1, line 9, please delete "60/639,110" and insert --60/939,110-- therefor;

Column 4, line 30, please delete the chemical structure

" 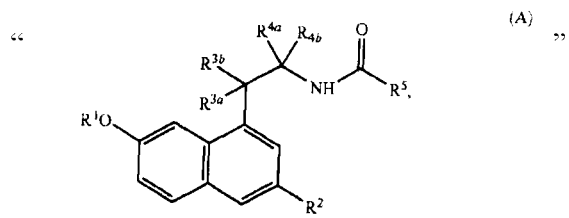 "

and insert -- 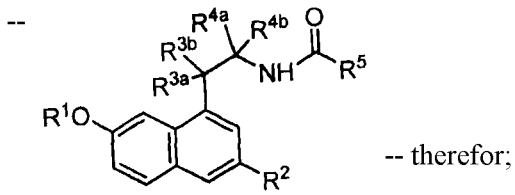 -- therefor;

Column 22, lines 9-16 (Claim 1), please delete the chemical structure

" 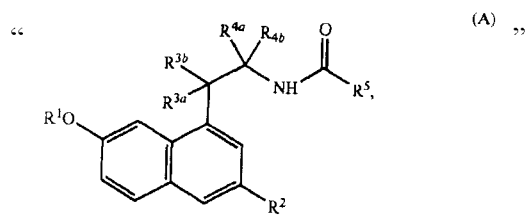 "

and insert

CERTIFICATE OF CORRECTION (continued)
U.S. Pat. No. 7,608,737 B2

-- 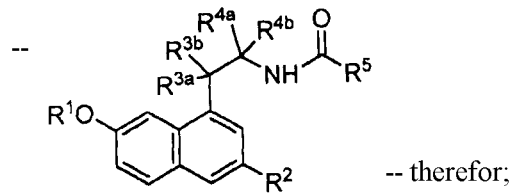 -- therefor;

Column 22, line 20 (Claim 1), please delete "$R_1$" and insert --$R^1$-- therefor;

Column 22, line 21 (Claim 1), please delete "$R_2$" and insert --$R^2$-- therefor;

Column 22, line 24 (Claim 1), please delete "$R^5$is" and insert --$R^5$ is-- therefor.

Signed and Sealed this

Sixteenth Day of March, 2010

David J. Kappos
*Director of the United States Patent and Trademark Office*